(12) United States Patent
Chen et al.

(10) Patent No.: US 11,105,712 B2
(45) Date of Patent: Aug. 31, 2021

(54) INTEGRATED VIBE/ODM FUSION AND TRENDING ANALYSIS FOR PROGNOSTIC HEALTH MANAGEMENT OF ENGINE BEARING

(71) Applicant: United Technologies Corporation, Farmington, CT (US)

(72) Inventors: Yan Chen, South Windsor, CT (US); Danbing Seto, Avon, CT (US); Sheridon Everette Haye, Mansfield, CT (US); Allan J. Volponi, West Simsbury, CT (US); Zaffir A. Chaudhry, S. Glastonbury, CT (US); Gregory S. Hagen, Glastonbury, CT (US); Lichu Zhao, Glastonbury, CT (US); Robert H. Luppold, West Newton, PA (US)

(73) Assignee: Raytheon Technologies Corporation, Farmington, CT (US)

( * ) Notice: Subject to any disclaimer, the term of this patent is extended or adjusted under 35 U.S.C. 154(b) by 543 days.

(21) Appl. No.: 15/946,987

(22) Filed: Apr. 6, 2018

(65) Prior Publication Data
US 2019/0310164 A1    Oct. 10, 2019

(51) Int. Cl.
*G01M 13/045*    (2019.01)
*G01N 33/28*    (2006.01)
(Continued)

(52) U.S. Cl.
CPC ...... *G01M 13/045* (2013.01); *G01N 33/2835* (2013.01); *F01D 25/18* (2013.01); *F02C 7/06* (2013.01)

(58) Field of Classification Search
CPC .. G01M 13/045; G01N 33/2835; F01D 25/18; F02C 7/06
(Continued)

(56) References Cited

U.S. PATENT DOCUMENTS

| 4,615,216 | A | * | 10/1986 | Vykoupil | ............... G01N 29/12 73/593 |
| 5,445,027 | A | * | 8/1995 | Zorner | ................... G01N 29/14 73/593 |

(Continued)

FOREIGN PATENT DOCUMENTS

WO    WO 2017/202753    11/2017

OTHER PUBLICATIONS

European Patent Office, European Search Report dated Aug. 26, 2019 in Application No. 19155541.6.

(Continued)

*Primary Examiner* — Lisa M Caputo
*Assistant Examiner* — Rose M Miller
(74) *Attorney, Agent, or Firm* — Snell & Wilmer L.L.P.

(57) ABSTRACT

A method for fault diagnosis of a bearing includes detecting, using an oil debris monitor (ODM) sensor, ODM data corresponding to an amount of debris flowing downstream from the bearing. The method also includes detecting, using a vibration sensor, vibration data corresponding to vibration of the bearing during use. The method also includes determining, by a controller, a vibration stage flag corresponding to a severity of damage of the bearing based on the vibration data. The method also includes determining, by the controller, a severity level of the damage of the bearing based on a combination of the vibration stage flag and the ODM data. The method also includes outputting, by an output device, the severity level.

15 Claims, 10 Drawing Sheets

(51) Int. Cl.
*F01D 25/18* (2006.01)
*F02C 7/06* (2006.01)

(58) Field of Classification Search
USPC .................................. 73/593, 587, 660, 659
See application file for complete search history.

(56) References Cited

U.S. PATENT DOCUMENTS

| | | | |
|---|---|---|---|
| 9,157,832 | B2 | 10/2015 | Uluyol et al. |
| 2006/0047403 | A1* | 3/2006 | Volponi ............. G05B 23/0221 |
| | | | 701/100 |
| 2006/0064291 | A1* | 3/2006 | Pattipatti ............ G05B 23/0251 |
| | | | 703/14 |
| 2007/0198215 | A1* | 8/2007 | Bonanni ............ G05B 23/0283 |
| | | | 702/183 |
| 2007/0277613 | A1 | 12/2007 | Iwatsubo et al. |
| 2008/0234964 | A1 | 9/2008 | Miyasaka et al. |
| 2011/0224917 | A1 | 9/2011 | Uluyol et al. |
| 2017/0315516 | A1 | 11/2017 | Kozionov et al. |
| 2019/0130294 | A1* | 5/2019 | Volponi ............. G05B 23/0254 |

OTHER PUBLICATIONS

European Patent Office, European Office Action dated Aug. 18, 2020 in Application No. 19155541.6.

* cited by examiner

| METHOD | CI | REFERENCE |
|---|---|---|
| 350 | TIME/FREQUENCY DOMAIN | INITIAL READING |
| 300 | TIME DOMAIN | INITIAL READING |
| 300 | FREQUENCY DOMAIN | INITIAL BACKGROUND LEVEL AROUND THE TARGET FAULT FREQUENCY |

FIG.4

| | METHOD | TIME DOMAIN CI | SPECTRAL DOMAIN CI |
|---|---|---|---|
| STAGE 2 | 300 | RMS | BDF, BPFO, BPFI |
| STAGE 3 | 350 | RMS | BDF, BPFO, BPFI, FTF |
| STAGE 4 | 350 | RMS | N |

| | TYPE | TIME DOMAIN CI THRESHOLD | SPECTRAL DOMAIN CI THRESHOLD |
|---|---|---|---|
| STAGE 2 | FIG. 3B | >T1 | >TH1 |
| STAGE 3 | FIG. 3A | >T2 | >TH2 |
| STAGE 4 | FIG. 3A | >T3 | >TH3 |

| | VIBE STAGE FLAG | ODM MASS INDEX (90%) | ODM MASS RATE (90%) | STATUS | ACTION |
|---|---|---|---|---|---|
| L1 | 2 | 1 | 1 | POSSIBLE DAMAGE INITIATED | ALERT |
| L2 | 2 | 1 | 2 | DAMAGE INITIATION CONFIRMED | ALERT |
| L3 | 3 | 1 | --- | DAMAGE PROGRESSION | WARNING |
| L4 | 3 | 2 | 1 | SEVERE DAMAGE | REPLACE |
| L5 | 3 | 2 | 2 | FAST GROW OF DAMAGE | APPROACHING TO FAILURE |
| L6 | 4 | 2 | --- | CLOSE TO FAILURE | SHUT DOWN |

FIG.11

| ALERT LEVEL | VIBE/ODM FUSION LEVEL | BEARING RESIDUAL LIFE | DAMAGE STATUS | ACTION |
|---|---|---|---|---|
| RED | L5 OR L6 | 0 | ACCELERATED SPALL PROGRESSION TO FAILURE | IMMEDIATE MAINTENANCE |
| ORANGE | L3 OR L4 | 4 TO 10 | STEADY SPALL PROGRESSION | MAINTENANCE WHEN CONVENIENT |
| YELLOW | L2 | 10 TO 40 | SPALL INITIATION CONFIRMED | PLACE ON WATCH |

FIG.12

INTEGRATED VIBE/ODM FUSION AND TRENDING ANALYSIS FOR PROGNOSTIC HEALTH MANAGEMENT OF ENGINE BEARING

GOVERNMENT LICENSE RIGHTS

This disclosure was made with Government support under Contract Number FA8650-09-D-2923-0023 awarded by the United States Air Force. The government has certain rights in the disclosure.

FIELD

The present disclosure relates generally to systems and methods for determining a status of bearing damage using, for example, vibration sensors and oil debris monitor (ODM) sensors.

BACKGROUND

Many engines include shafts that transfer torque from a power source to a component that propels the vehicle or otherwise powers the vehicle. For example, a gas turbine engine may include a shaft that transfers torque from a turbine section to a fan to generate thrust. As another example, a gasoline engine may include one or more shafts that transfers torque from the engine to wheels of a corresponding vehicle. Many such shafts are supported by bearings. In response to bearing damage, the corresponding engine may operate improperly.

SUMMARY

Described herein is a method for fault diagnosis and prognosis of a bearing. The method includes detecting, using an oil debris monitor (ODM) sensor, ODM data corresponding to an amount of debris flowing downstream from the bearing. The method also includes detecting, using a vibration sensor, vibration data corresponding to vibration of the bearing during use. The method also includes determining, by a controller, a vibration stage flag corresponding to a severity of damage of the bearing based on the vibration data. The method also includes determining, by the controller, a severity level of the damage of the bearing based on a combination of the vibration stage flag and the ODM data. The method also includes outputting, by an output device, the severity level.

In any of the foregoing embodiments, determining the vibration stage flag includes determining the vibration stage flag based on a time-domain analysis of the vibration data and a frequency-domain analysis of the vibration data.

In any of the foregoing embodiments, determining the vibration stage flag based on the time-domain analysis of the vibration data includes determining the vibration stage flag based on root mean square (RMS), Kurtosis, and Skewness values of the vibration data.

In any of the foregoing embodiments, determining the vibration stage flag based on the frequency-domain analysis of the vibration data includes analyzing at least one of a fundamental train frequency of the bearing, a ball pass outer race frequency, a ball pass inner race frequency, or a ball defect frequency.

In any of the foregoing embodiments, determining the vibration stage flag further includes determining a time flag corresponding to the time-domain analysis of the vibration data, determining a frequency flag corresponding to the frequency-domain analysis, and setting the vibration stage flag if either the time flag or the frequency flag is set.

In any of the foregoing embodiments, determining the vibration stage flag may include computing a resonance frequency and a frequency band of the resonance frequency, bandpass filtering the vibration data to obtain a filtered signal, demodulating the filtered signal to obtain a demodulated signal, and performing time-domain and frequency-domain analyses of the demodulated signal.

In any of the foregoing embodiments, determining the vibration stage flag based on the time-domain analysis of the vibration data includes normalizing the vibration data in a time domain, and wherein determining the vibration stage flag based on the frequency-domain analysis of the vibration data includes normalizing the vibration data in a frequency domain.

In any of the foregoing embodiments, detecting the vibration data includes detecting vibration data from multiple vibration sensors; and determining the vibration stage flag based on the vibration data includes: determining a vibration stage flag based on the vibration data from each of the vibration sensors, and determining the vibration stage flag to be a maximum value of all of the vibration stage flags determined from each of the vibration sensors.

In any of the foregoing embodiments, determining the vibration stage flag based on the vibration data includes comparing the vibration data to a reference vibration data that was detected during an initial use of the bearing.

|Any of the foregoing embodiments may also include storing, in a memory, a decision table; and determining, by the controller, a residual life of the bearing by comparing the combination of the vibration stage flag and the ODM data to the decision table.|$_{[JT1]}$ Also disclosed is a method for fault diagnosis of a bearing used in an engine. The method includes detecting, using an oil debris monitor (ODM) sensor, ODM data corresponding to an amount of debris flowing downstream from the bearing. The method also includes detecting, using a vibration sensor, vibration data corresponding to vibration of the bearing during use. The method also includes determining, by a controller, a vibration stage flag corresponding to a severity of damage of the bearing based on a time-domain analysis of the vibration data and a frequency-domain analysis of the vibration data. The method also includes determining, by the controller, a severity level of the damage of the bearing based on a combination of the vibration stage flag and the ODM data. The method also includes outputting, by an output device, the severity level.

In any of the foregoing embodiments, determining the vibration stage flag based on the time-domain analysis of the vibration data includes determining the vibration stage flag based on root mean square (RMS), Kurtosis, and Skewness values of the vibration data.

In any of the foregoing embodiments, determining the vibration stage flag based on the frequency-domain analysis of the vibration data includes analyzing at least one of a fundamental train frequency of the bearing, a ball pass outer race frequency, a ball pass inner race frequency, or a ball defect frequency.

In any of the foregoing embodiments, determining the vibration stage flag further includes determining a time flag corresponding to the time-domain analysis of the vibration data, determining a frequency flag corresponding to the frequency-domain analysis, and setting the vibration stage flag if either the time flag or the frequency flag is set.

In any of the foregoing embodiments, determining the vibration stage flag may include computing a resonance frequency and a frequency band of the resonance frequency, bandpass filtering the vibration data to obtain a filtered signal, demodulating the filtered signal to obtain a demodulated signal, and performing time-domain and frequency-domain analyses of the demodulated signal.

In any of the foregoing embodiments, determining the vibration stage flag based on the time-domain analysis of the vibration data includes normalizing the vibration data in a time domain, and wherein determining the vibration stage flag based on the frequency-domain analysis of the vibration data includes normalizing the vibration data in a frequency domain.

In any of the foregoing embodiments, detecting the vibration data includes detecting vibration data from multiple vibration sensors; and determining the vibration stage flag based on the vibration data includes: determining a vibration stage flag based on the vibration data from each of the vibration sensors, and determining the vibration stage flag to be a maximum value of all of the vibration stage flags determined from each of the vibration sensors.

Also disclosed is a system for fault diagnosis of bearings. The system includes an oil debris monitor (ODM) sensor configured to detect ODM data corresponding to an amount of debris flowing downstream from a bearing. The system also includes a vibration sensor configured to detect vibration data corresponding to vibration of the bearing during use. The system also includes a controller. The controller is designed to determine a vibration stage flag corresponding to a severity of damage of the bearing based on the vibration data, and to determine a severity level of the damage of the bearing based on a combination of the vibration stage flag and the ODM data. The system also includes an output device configured to output the severity level.

In any of the foregoing embodiments, the controller is further configured to determine the vibration stage flag based on a time-domain analysis of the vibration data and a frequency-domain analysis of the vibration data.

In any of the foregoing embodiments, the time-domain analysis of the vibration data is based on root mean square (RMS), Kurtosis, and Skewness values of the vibration data.

The foregoing features and elements are to be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

BRIEF DESCRIPTION OF THE DRAWINGS

The subject matter of the present disclosure is particularly pointed out and distinctly claimed in the concluding portion of the specification. A more complete understanding of the present disclosure, however, is best be obtained by referring to the detailed description and claims when considered in connection with the drawing figures, wherein like numerals denote like elements.

DETAILED DESCRIPTION

The detailed description of exemplary embodiments herein makes reference to the accompanying drawings, which show exemplary embodiments by way of illustration and their best mode. While these exemplary embodiments are described in sufficient detail to enable those skilled in the art to practice the inventions, it should be understood that other embodiments may be realized and that logical, chemical and mechanical changes may be made without departing from the spirit and scope of the inventions. Thus, the detailed description herein is presented for purposes of illustration only and not of limitation. For example, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact. Where used herein, the phrase "at least one of A or B" can include any of "A" only, "B" only, or "A and B."

Figure 1:
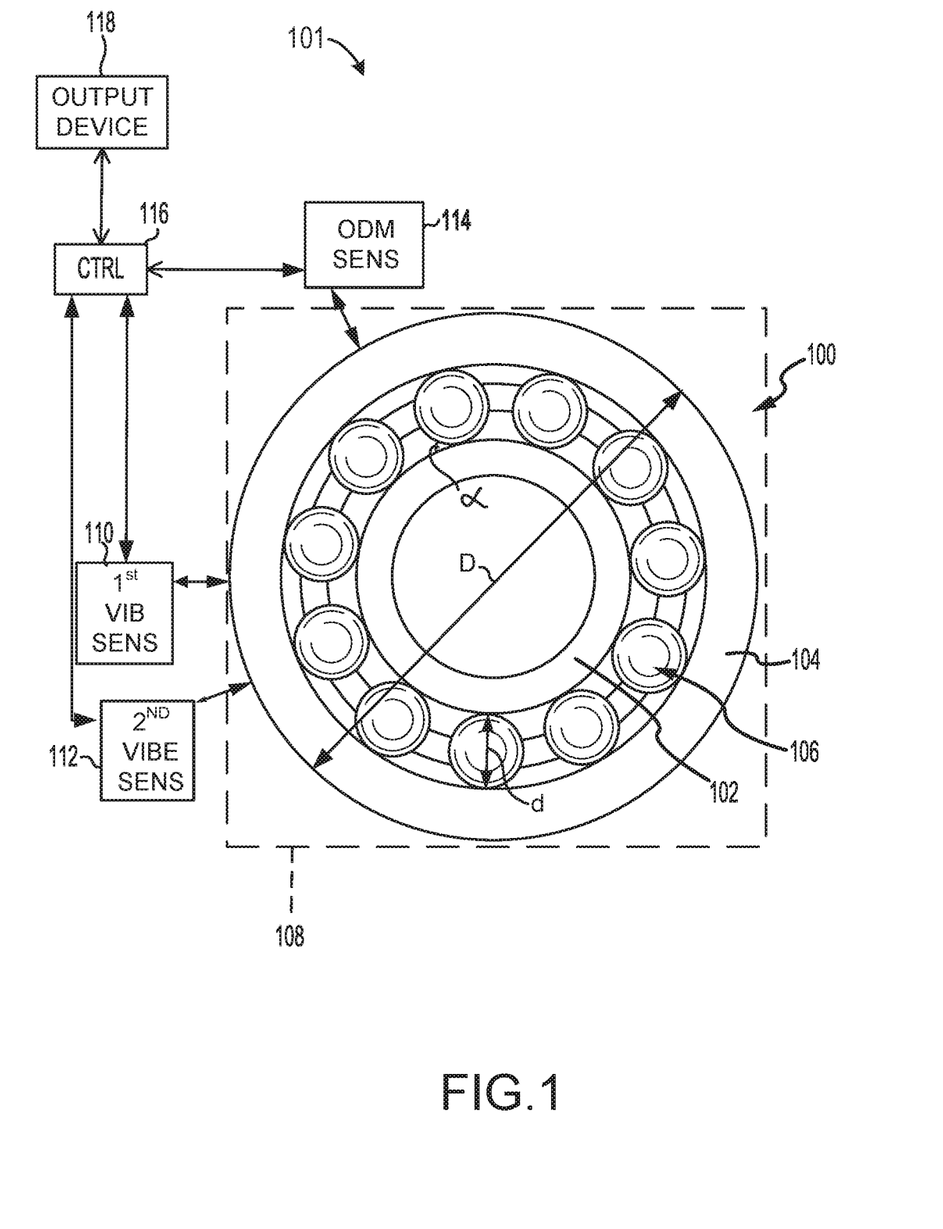
FIG. 1 illustrates a system for fault diagnosis of a bearing, in accordance with various embodiments.

With reference to FIG. 1, a system 101 for fault diagnosis of a bearing 100 is shown. The system 101 includes the bearing 100, an oil debris monitor (ODM) sensor 114, a first vibration sensor 110, a second vibration sensor 112, a controller 116, and an output device 118. While two vibration sensors are illustrated, the system 101 may include any quantity of vibration sensors without departing from the scope of the present disclosure.

The bearing 100 may be located within a cage 108 and may include an inner race 102, an outer race 104, and multiple balls 106 positioned between the inner race 102 and the outer race 104. The bearing 100 may fail in any of a number of manners. For example, the inner race 102 may become damaged, the outer race 104 may become damaged, or one or more of the balls 106 may become damaged. In various embodiments, the cage 108 may likewise become damaged such that the bearing 100 may undesirably move relative to the cage 108.

The ODM sensor 114 may include any sensor capable of monitoring debris flowing downstream from the bearing 100. For example, the ODM sensor 114 may detect one or more of a total mass of debris detected downstream from the bearing 100, a rate of debris accumulation downstream from the bearing 100, or the like. For example, the ODM sensor 114 may include a mass sensor, a pressure sensor, a liquid level sensor, or the like.

The vibration sensors 110, 112 may include any sensor capable of detecting vibrations generated by the bearing 100. For example, the vibration sensors 110, 112 may include one or more of an accelerometer, a velocity sensor, a proximity probe, a laser displacement sensor, or the like.

The controller 116 may include one or more logic device such as one or more of a central processing unit (CPU), an accelerated processing unit (APU), a digital signal processor (DSP), a field programmable gate array (FPGA), an application specific integrated circuit (ASIC), or the like. In various embodiments, the controller 116 may further include any non-transitory memory known in the art. The memory may store instructions and data usable by the logic device to perform operations.

The output device 118 may include any output device such as a display, a speaker, a touchscreen, a memory, or the like. The output device 118 may receive data from the controller 116 corresponding to the health of the bearing 100, and may output data that indicates the health status of the bearing 100.

The bearing 100 may be used, for example, to facilitate rotation of a shaft of an engine. For example, the shaft may be a main shaft of an engine, such as a gas turbine engine, that transfers rotational energy from a turbine to at least one of a fan, a compressor, or helicopter blades.

Figure 2:
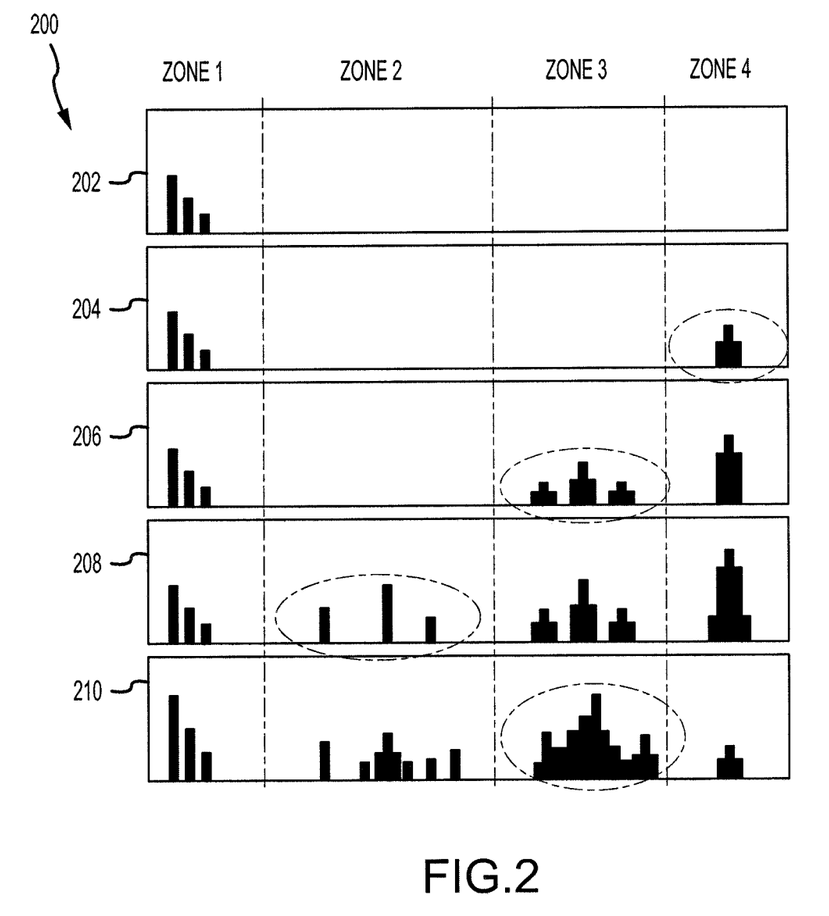
FIG. 2 illustrates various stages of bearing damage progression, in accordance with various embodiments.

Referring now to FIG. 2, progression of bearing damage may be generally categorized into four stages. The categorization may be based on an amplitude of signals detected at various frequencies. FIG. 2 is a plot 200 illustrating amplitude (along the Y axis) of signals at various frequencies (along the X axis) for various stages of bearing damage. Normal bearing operation 202 is shown as having a signal located in zone 1 only.

Stage 1 bearing damage 204 is shown as having the signal in zone 1 along with an additional signal in zone 4. The signal in zone 4 may be formed by spike energy produced by micro defects in the bearing and may have an ultrasonic frequency. Stage 2 bearing damage 206 is shown as having signals in zones 1, 3, and 4. The signal in zone 3 may include resonance vibration that is excited by varying defects. Stage 3 bearing damage 208 is shown as having signals in each of zones 1, 2, 3, and 4. Stage 4 bearing damage 210 is shown as having signals in each of the zones that have a greater amplitude or root mean square (RMS), Kurtosis, and Skewness values in one or more of zones 2, 3, or 4.

Figure 3A:
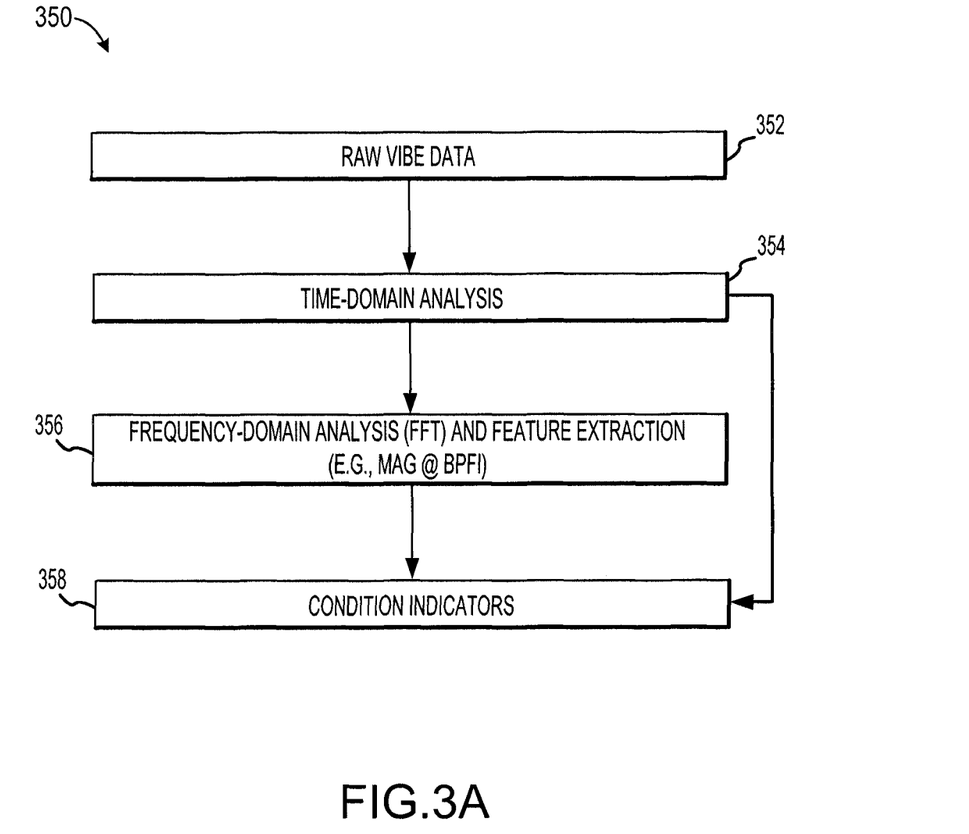
FIG. 3A is a flowchart illustrating a method for fault diagnosis of a bearing, in accordance with various embodiments.

Referring now to FIG. 3A, a method 350 may be used to detect bearing defects that have reached stage 3 bearing damage or stage 4 bearing damage. The method 350 may be performed by a controller, such as the controller 116 of FIG. 1.

The method 350 begins in block 352 where vibration data is acquired by a vibration sensor. The method 350 may include a time-domain analysis of the vibration data in block 354 and a frequency-domain analysis in block 356. The time domain analysis and the frequency domain analysis may provide certain condition indicators which may be compared to reference values (i.e., reference condition indicators) to determine whether the bearing damage has reached a given stage.

The time domain analysis in block 354 may include determining at least one of a root mean square (RMS) value, a Kurtosis value, or a Skewness value of the vibration data, and comparing the value(s) to reference value(s). The frequency domain analysis in block 356 may include, for example, a magnitude of a signal at a given frequency. For example, the frequency may be referred to as a defect frequency and may correspond to at least one of a frequency that is associated with damage to the bearing cage (a fundamental train frequency of the bearing, FTF), a frequency that is associated with damage to the bearing inner race (a ball pass inner race frequency, BPFI), a frequency that is associated with damage to the bearing outer race (a ball pass outer race frequency, BPFO), or a frequency that is associated with damage to one or more balls of the bearing (a ball defect frequency, BDF).

The defect frequencies may be calculated using the following equations 1, 2, 3, and 4 below.

$$FTF = f_r\left(1 - \frac{d}{D}\cos\alpha\right)\frac{1}{2} \qquad \text{Equation 1}$$

$$BPFI = \frac{N}{2}f_r\left(1 + \frac{d}{D}\cos\alpha\right) \qquad \text{Equation 2}$$

$$BPFO = \frac{N}{2}f_r\left(1 - \frac{d}{D}\cos\alpha\right) \qquad \text{Equation 3}$$

$$BDF = \frac{D}{d}f_r\left[1 - \left(\frac{d}{D}\cos\alpha\right)^2\right] \qquad \text{Equation 4}$$

In the above equations and with brief reference to FIG. 1, D represents the pitch diameter of the bearing, d is the ball diameter, a is the contact angle, N is the number of balls and $f_r$ is the rotating frequency of the shaft that is supported by the bearing.

Although the method 350 of FIG. 3A may be used to detected stage 3 and stage 4 bearing defects, the method 350 may be insufficient for detecting stage 2 bearing defects. In that regard and referring to FIG. 3B, a method 300 may be used to detect stage 2 bearing defects. The method 300 may be performed by a controller, such as the controller 116 of FIG. 1. The method 300 may include a preprocessing phase 302, an enveloping phase 304, and a feature identification and condition indicator phase 306.

Figure 3B:
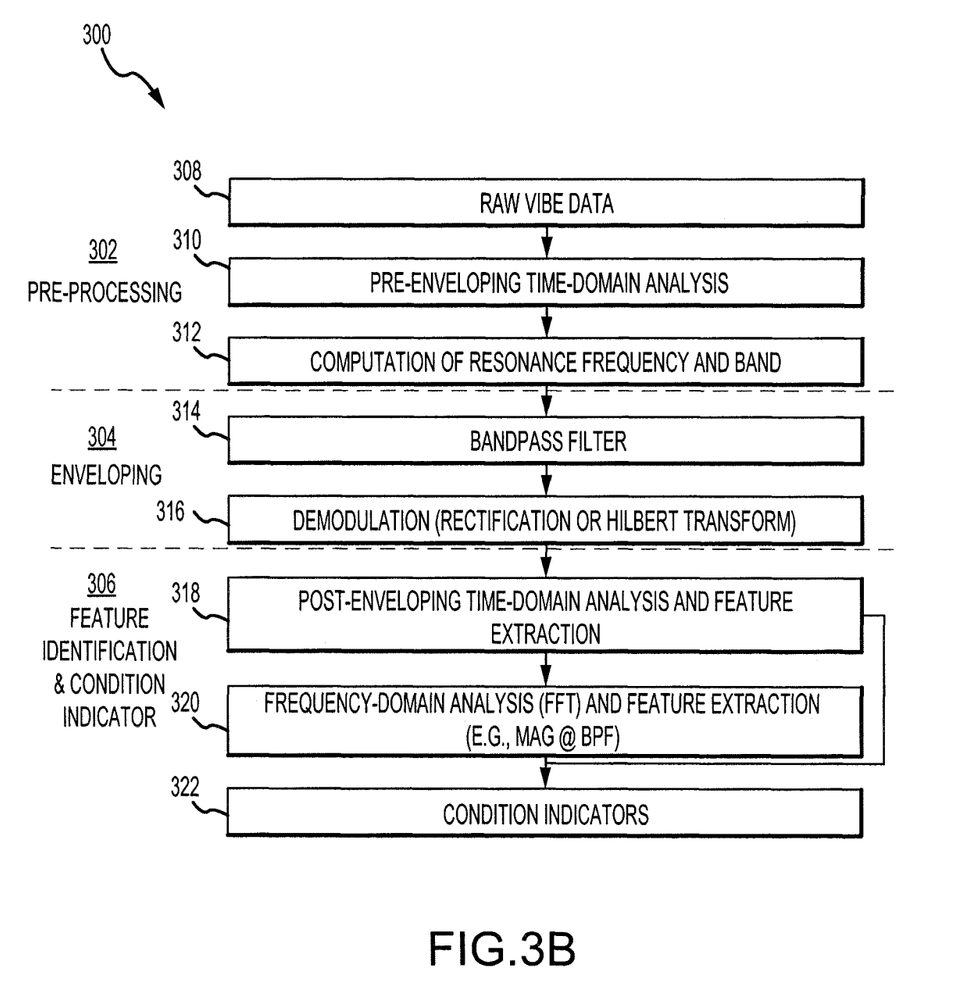
FIG. 3B is a flowchart illustrating an advanced method for fault diagnosis of a bearing, and accordance with various embodiments.

In block 308, vibration data may be acquired by one or more vibration sensor associated with the bearing. In block 310, a time domain analysis of the vibration data may be performed. The time-domain analysis may include, for example, comparing a RMS value of the vibration data to a reference RMS value.

In block 312, a resonance frequency and band of the bearing vibration data may be computed. The band may be selected to be large enough to include one or more of the FTF, BPFO, BPFI, or BDF. In various embodiments, the band may be selected to be large enough to include all four of these frequencies.

In block 314, the vibration data may be passed through a bandpass filter that captures the signal at the resonance frequency and band that were determined in block 312. The results of blocks 314 may be a filtered signal that includes the vibration data at one or more of the FTF, BPFO, BPFI, or BDF.

In block 316, the vibration data may be demodulated in order to recover the envelope of the vibration data. The demodulation may be performed, for example, using rectification or a Hilbert transformation. The result of block 316 may be a demodulated signal.

In block 318, the controller may perform a post-enveloping time domain analysis and feature extraction function, including but not limited to condition indicators such as RMS value, peak vibe data, Kurtosis values, and Skewness values. These condition indicators may be normalized to some reference values to address application to application variations. The time domain analysis performed in block 318 may be of higher quality than the time domain analysis performed in block 310 because the demodulated signal that is analyzed in block 318 has been filtered to remove at least some noise. Thus, the calculated RMS value may correspond to the value at the defect frequency.

In block 320, the controller may perform a frequency domain analysis and feature extraction of the demodulated signal. For example, the demodulated signal may be converted to the frequency domain using a Fourier transfer (FT), a fast Fourier transfer (FFT), or the like. The frequency domain analysis may include determining the magnitude of the signal at one or more of the FTF, BPFO, BPFI, or BDF. In various embodiments, the frequency domain analysis may also include comparing the magnitude at each of the defect frequencies to a reference magnitude.

In block 322, condition indicators may be identified from the time domain analysis from block 310, the time domain analysis from block 318, and the frequency domain analysis in block 320. The condition indicators may include such information as whether the RMS value exceeds a reference RMS value, a magnitude of the RMS value, whether a signal is detected at one or more of the defect frequencies, a magnitude of the signal at one or more of the defect frequencies, or the like.

Each engine in which a bearing may be used, and each bearing, may be unique. The uniqueness may be due to design differences, manufacturing tolerances, or the like. In that regard, it may be desirable to normalize the condition indicators for each bearing used in each engine to identify the reference values (i.e., reference condition indicators) for each bearing of each engine.

Figure 4:
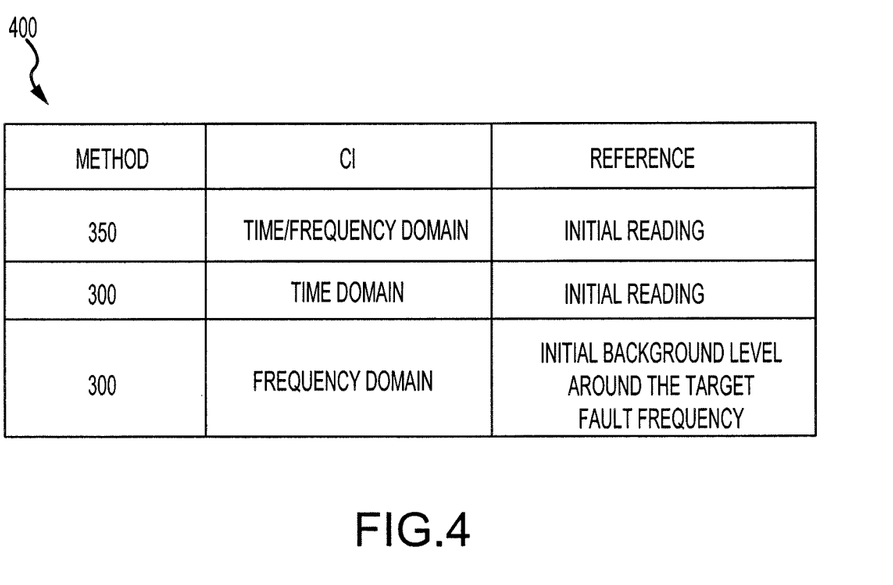
FIG. 4 is a chart illustrating a source of reference condition indicators, in accordance with various embodiments.

Referring to FIG. 4, a chart 400 illustrates an exemplary source of the normalized reference values (i.e., reference vibration data). For the method 350 of FIG. 3A, the reference condition indicators for both the time domain and the frequency domain condition indicators may be obtained by an initial reading of the vibration sensor or vibration sensors during an initial use of the bearing. For the method 300 of FIG. 3B, the reference condition indicators for the time domain condition indicators may likewise be obtained by an initial reading of the vibration sensor or vibration sensors during the initial use of the bearing. For the method 300 of FIG. 3B, the reference condition indicators for the frequency domain condition indicators may be obtained by measuring or detecting initial background levels at the target fault frequencies (the defect frequencies). For example, the level around the defect frequency (i.e., the level in the frequency range of the defect frequency +/−50 hertz (50 Hz)) may be used as the reference, and the level may include about 90 percent (90%) of the data within that range, excluding data points with spiky magnitude at the defect frequency.

Figure 5:
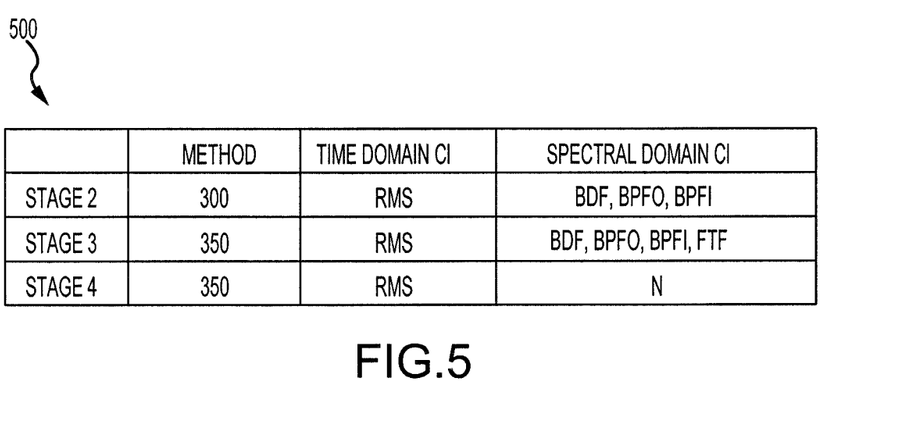
FIG. 5 is a chart illustrating condition indicators to be used for fault diagnosis of a bearing based on a bearing damage stage, in accordance with various embodiments.

Turning now to FIG. 5, a chart 500 illustrates which condition indicators may be used to identify each stage of bearing damage. Stage 2 bearing damage may be identified using the method 300 of FIG. 3B with RMS, Kurtosis, and Skewness values as the time domain condition indicators of the demodulated signal and BDF, BPFO, and BPFI of the demodulated signal as the frequency domain condition indicators. Stage 3 bearing damage may be identified using the method 350 of FIG. 3A with RMS of the raw signal as the time domain condition indicator and BDF, BPFO, BPFI, and FTF of the raw signal as the frequency domain condition indicators. Stage 4 bearing damage may be identified using the method 350 of FIG. 3A again with RMS of the raw signal as the time domain condition indicator and shaft speed N of the raw signal as the frequency domain condition indicators.

Figure 6:
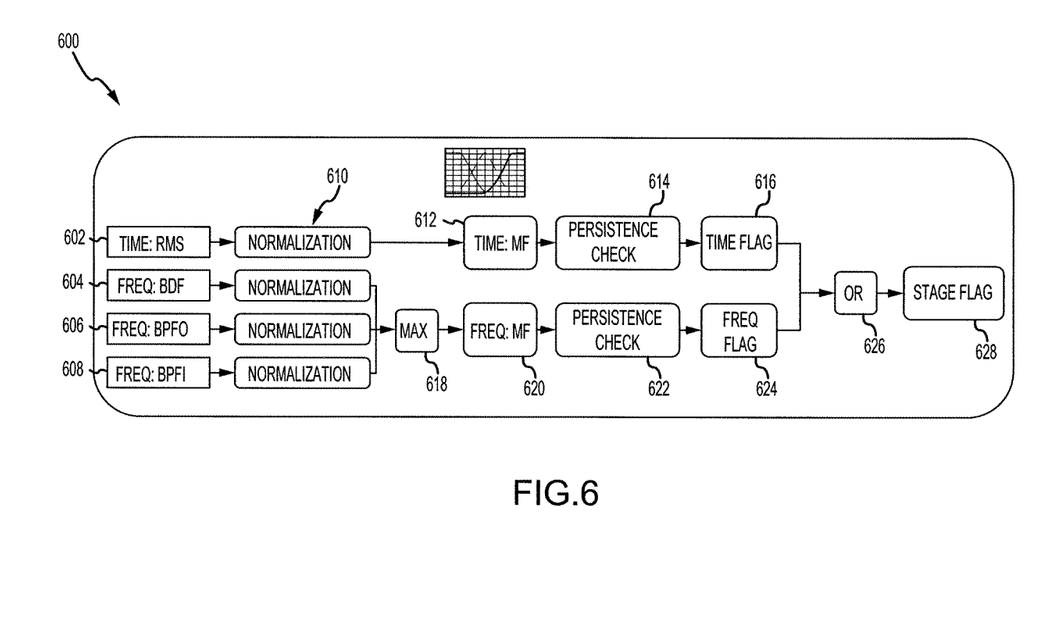
FIG. 6 is a flowchart illustrating a method for identifying a vibration stage flag of a bearing, in accordance with various embodiments.

Turning now to FIG. 6, a method 600 for identifying or determining a vibration stage flag 628 that corresponds to a severity of the bearing fault is shown. The method 600 may be evaluated for all stages 2, 3, and 4, and may produce a binary result for each bearing damage stage, with a logic True indicating that substantial vibration evidence from the vibration data exists to support a conclusion of bearing damage at the corresponding stage.

The method 600 may determine the condition indicators of RMS 602 in the time domain along with the BDF 604, BPFO 606, and BPFI 608. In various embodiments, the method 600 may also determine Kurtosis and Skewness values in the time domain, and the FTF and shaft speed N in the frequency domain. The condition indicators may be computed using the method 300 with the demodulated signals for determining stage 2 bearing damage, or by the method 350 with the raw vibe data for determining stages 3 and 4 bearing damage.

Each of the RMS 602, the BDF 604, the BPFO 606, and the BPFI 608 may be normalized using a normalization routine 610.

In block 612, the normalized RMS 610 may be fed into a membership function to evaluate the damaged value. The damage value may range from 0 to 1. A persistence check may be performed in block 614 to reduce the likelihood of an intermittent anomaly value creating a false result. For example, if 90% of the values received by the persistence check 614 exceeds 0.9 indicating stage 2 bearing damage, then the persistence check may be satisfied, and the time flag 616 may be set to logic True to confirm the determination of stage 2.

In block 618, a maximum of the normalized BDF value, BPFO value, BPFI value, (or FTF value) may be selected. The maximum value may be fed into a frequency membership function 620 to evaluate the damaged value. For example, the membership function 620 may compare the amplitude at one of the defect frequencies to a reference value. The results of the frequency membership function 620 may be fed to a persistence check 622 to reduce the likelihood of intermittent anomalies creating false results. A frequency flag 624 may be set to logic True to confirm the stage that was determined in the membership function 620.

In block 626, the controller may set the stage flag 628 to logic True if either the time flag 616 or the frequency flag 624 is set to logic True.

Figure 7:
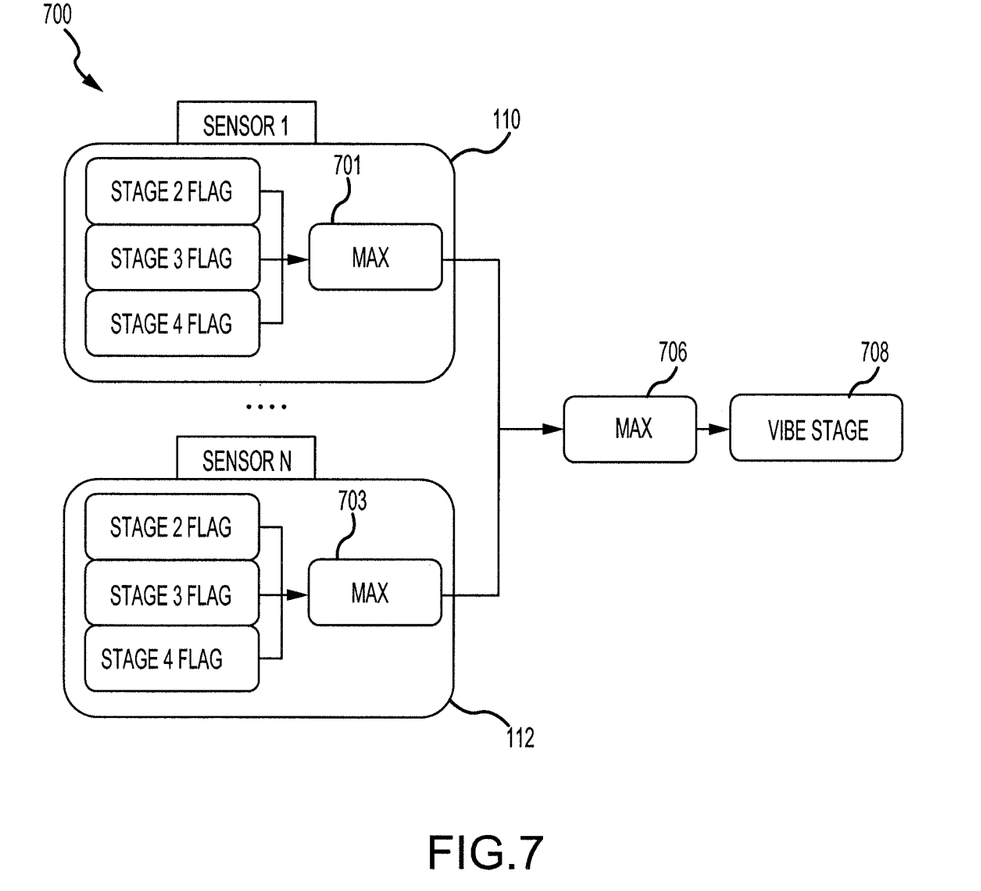
FIG. 7 is a flowchart illustrating a method for identifying a vibration stage flag of a bearing using multiple sensors, in accordance with various embodiments.

Referring now to FIGS. 1 and 7, the first vibration sensor 110 may detect first vibration data, and the second vibration sensor 112 may detect second vibration data. The controller 116 may determine a first vibration flag 701 (such as by using a method similar to the method 600 of FIG. 6) based on the first vibration data, and the controller 116 may also determine a second vibration flag 703 based on the second vibration data. While illustrated with two vibration sensors, the method 700 is applicable to systems that include more than two vibration sensors. The MAX selection 701 and 703 respectively result in a value corresponding to the highest stage that is set to logic True using a method similar to the method 600 of FIG. 6. The controller 116 may identify a maximum bearing damage stage 706, and may set the vibration stage flag 708 to be equal to the maximum bearing damage stage 706. In that regard, the controller 116 may assess the bearing damage based on the highest stage prediction among all sensors associated with the bearing.

Figure 8:
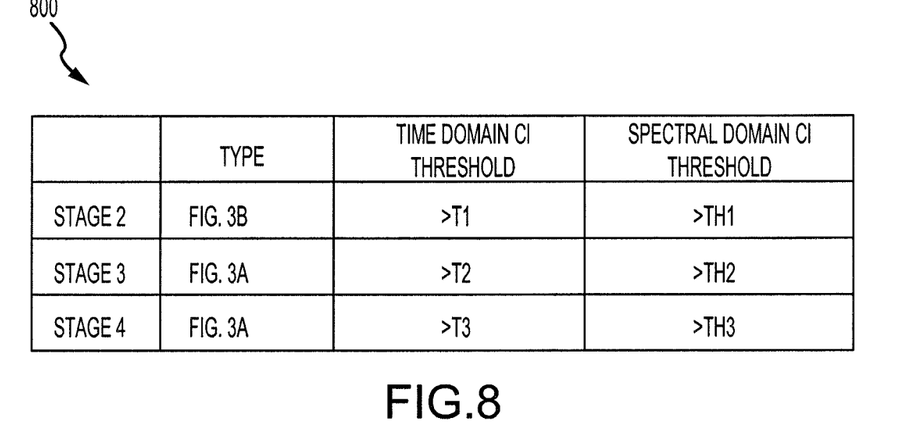
FIG. 8 is a table illustrating exemplary condition indicators thresholds, in accordance with various embodiments.

Referring now to FIG. 8, an exemplary table 800 illustrates various condition indicator thresholds for the time domain and the frequency domain for each stage of bearing damage. For example, a controller may identify that a bearing is experiencing stage 3 bearing damage if the time domain condition indicator (such as a normalized RMS value) is greater than T2. Similarly, the controller may identify that the bearing is experiencing stage 2 bearing damage if the frequency domain condition indicator (such as in amplitude at a given defect frequency or a normalized amplitude at the given defect frequency) is greater than TH1. In various embodiments, the table 800 may include multiple condition indicator thresholds for each stage of bearing damage in the frequency domain, each corresponding to one of the defect frequencies (e.g., a first threshold for the BDF, a second threshold for the BPFI, etc.).

Figure 9:
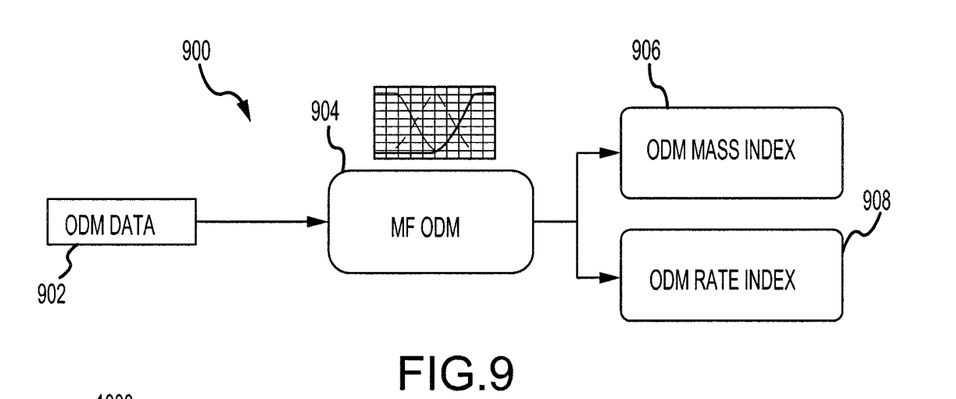
FIG. 9 is a flowchart illustrating a method for identifying an ODM mass index and an ODM rate index, in accordance with various embodiments.

Referring now to FIG. 9, a method 900 may be used to identify an amount and a rate of debris that is flowing downstream from the bearing. It is assumed that the debris flowing downstream from the bearing corresponds to the debris that have been liberated from the bearing due to damage to the bearing.

In block 902, ODM data 902 represents ODM condition indicators processed from the ODM sensor signal, which may include but is not limited to debris particle and mass accumulations. Illustrated in FIG. 9 is the debris mass accumulation. The ODM data may be received by an ODM membership function 904. The membership function 904 of the ODM may compare the ODM data to an engine based threshold or may otherwise analyze the ODM data 902.

The ODM membership function 904 may output an ODM mass index 906 and an ODM rate index 908. The ODM mass index 906 and the ODM rate index 908 may or may not be normalized to the given bearing and/or the given engine in which the bearing is used. The ODM mass index 906 may correspond to a total amount of debris (i.e., a sum) that has been detected by the ODM sensor during the life of the bearing. The ODM rate index 908 may correspond to a rate at which the debris is flowing downstream from the bearing (such as in a unit of milligram per unit of time).

Figure 10:
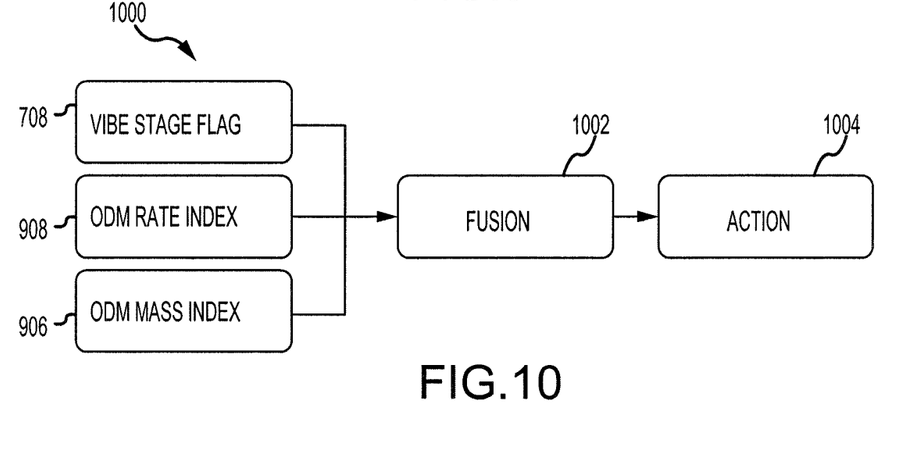
FIG. 10 is a flowchart illustrating a fusion algorithm for identifying a severity level of bearing damage based on vibration data and ODM data, in accordance with various embodiments.

Turning now to FIG. 10, a method 1000 may be used by a controller, such as the controller 116 of FIG. 1, to identify a health status of a bearing, such as the bearing 100 of FIG. 1, based on vibration data and ODM data. The method 1000 may include analyzing the vibration stage flag 708 (which may be determined using the method 700 of FIG. 7), the ODM rate index 908 (which may be determined using the method 900 of FIG. 9), and the ODM mass index 906 (which may be determined using the method 900 of FIG. 9). The method 1000 includes a fusion 1002 of the vibration stage flag 708, the ODM rate index 908, and the ODM mass index 906. The fusion 1002 may be performed using a lookup table or chart (such as the lookup table 1100 of FIG. 11). The fusion 1002 may output an action 1004 which may include no action (if the bearing is undamaged), may include transmitting a message to a remote device, or controlling an output device to output data indicating a severity level of the bearing damage.

Figure 11:
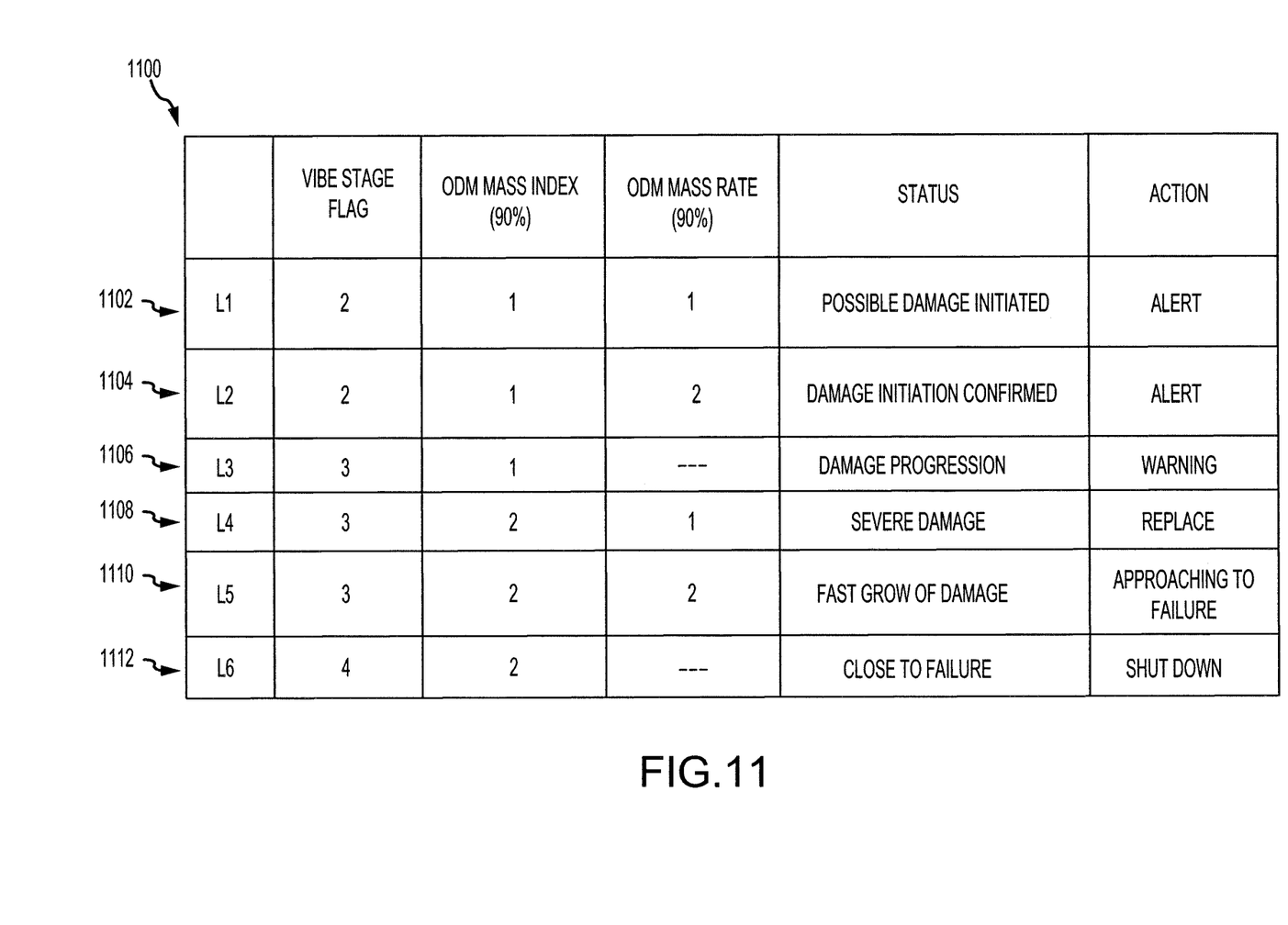
FIG. 11 illustrates a decision table that may be used to identify a severity level of bearing damage, in accordance with various embodiments.

Turning now to FIG. 11, the lookup table 1100 may be used as the fusion algorithm 1002 of FIG. 10. In particular, a controller may compare a determined vibration stage flag, an ODM mass index, and an ODM mass rate to the lookup table 1100 to determine the severity level of the bearing damage.

A first row 1102 corresponds to a severity level L1. The controller may determine that the severity level is L1 in response to the vibration stage flag being set to 2, the ODM mass index being set to 1 (i.e., the ODM mas index may reach a first threshold), and the ODM mass rate being set to 1 (i.e., the ODM mass rate may reach a first threshold). The severity level L1 may indicate that bearing damage has potentially been initiated. In response to determining that the severity level is L1, the controller may control an output device to output an alert, which may include an indication of the severity level (L1), or may include a color-coded signal (such as a yellow light).

A second row 1104 corresponds to a severity level L2. The controller may determine that the severity level is L2 in response to the vibration stage flag being set to 2, the ODM mass index being set to 1, and the ODM mass rate being set to 2. The controller may determine that the bearing damage status has proceeded from L1 to L2 if the above conditions remain satisfied for a predetermined amount of time (such as 5 minutes, 10 minutes, 30 minutes, or the like). The severity level L2 may indicate that an initial bearing damage is confirmed. In response to determining that the severity level is L2, the controller may control the output device to output an alert, which may include the indication of the severity level (L2) or may include a color-coded signal (such as a yellow light).

A third row 1106 corresponds to a severity level L3. The controller may determine that the severity level is L3 in response to the vibration stage flag being set to 3 and the ODM mass index being set to 1. The ODM mass rate may be unset (i.e., the ODM mass rate may not reach a threshold) or may be irrelevant for determining L3 severity level. The severity level L3 may indicate that damage of the bearing has progressed beyond L2. In response to determining that the severity level is L3, the controller may control the output device to output a warning, which may include the indication of the severity level (L3) or may include a color-coded signal (such as an orange light).

A fourth row 1108 corresponds to a severity level L4. The controller may determine that the severity level is L4 in response to the vibration stage flag being set to 3, the ODM mass index being set to 2 (the ODM mass index may reach or exceed a second threshold), and the ODM mass rate being set to 1. The severity level L4 may indicate that the bearing has experienced relatively severe damage. In response to determining that the severity level is L4, the controller may control the output device to output another warning, which may include the indication of the severity level (L4) and a message to have the bearing replaced as soon as is convenient, or may include a color-coded signal (such as an orange or red light).

A fifth row 1110 corresponds to a severity level L5. The controller may determine that the severity level is L5 in response to the vibration stage flag being set to 3, the ODM mass index being set to 2, and the ODM mass rate being set to 2. The severity level L5 may indicate that the bearing is experiencing a relatively fast growth of the damage and may be approaching failure. In response to determining that the severity level is L5, the controller may control the output device to output another warning, which may include the indication of the severity level (L5) or a message to have the bearing replaced as soon as possible, or may include a color-coded signal (such as a red light). In various embodiments, the controller may control the output device to output a message indicating that the aircraft should be grounded until the faulty bearing is replaced.

A sixth row 1112 corresponds to a severity level L6. The controller may determine that the severity level is L6 in response to the vibration stage flag being set to 4 and the ODM mass index being set to 2, regardless of the ODM mass rate. The severity level L6 may indicate that the bearing is near failure and the aircraft should be taken to the nearest possible landing spot for replacement of the bearing. In response to determining that the severity level is L6, the controller may control the output device to output another warning, which may include the indication of the severity level (L6) or a message to ground the aircraft as soon as possible, or may include a color-coded signal (such as a red light).

Figure 12:
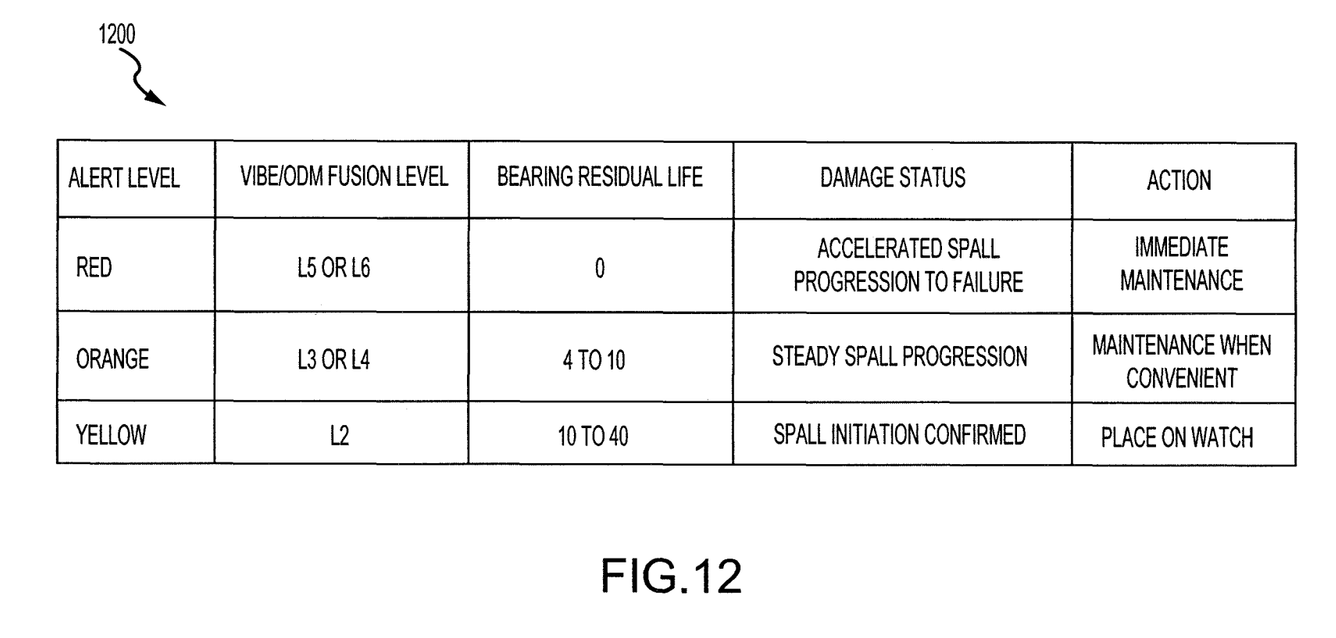
FIG. 12 illustrates a decision table that may be used to identify a residual life of a bearing, in accordance with various embodiments.

Turning now to FIG. 12, an exemplary lookup table 1200 may be used to identify an action to be taken based on a determined severity level of bearing damage. For example, if the severity level is L2, the controller may control an output device to output a signal that places the bearing on a watch, indicating that the bearing may be experiencing damage. The controller may further use the lookup table 1200 to identify that a residual life of the bearing is between 10 and 40 hours in response to determining that the severity level is L2. If the severity level is L3 or L4, the controller may control an output device to output a signal indicating that the bearing should be taken for maintenance when convenient. The controller may further use the lookup table 1200 to identify that the residual life of the bearing is between 4 and 10 hours. If the severity level is L5 or L6, the controller may control an output device to output a signal indicating that maintenance should be performed immediately to replace the bearing. The controller may further use the lookup table 1200 to identify that the bearing residual life is near 0 hours.

The controller may at any point control the output device to output the residual life of the bearing.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the inventions. The scope of the invention is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment", "an embodiment", "various embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f), unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

The invention claimed is:

1. A method for fault diagnosis of a bearing, comprising:
   detecting, using an oil debris monitor (ODM) sensor, ODM data corresponding to an amount of debris flowing downstream from the bearing;
   detecting, using a vibration sensor, vibration data corresponding to vibration of the bearing during use;
   determining, by a controller, a vibration stage flag corresponding to a severity of damage of the bearing based on the vibration data;
   determining, by the controller, a severity level of the damage of the bearing based on a combination of the vibration stage flag and the ODM data; and
   outputting, by an output device, the severity level, wherein:
   determining the vibration stage flag based on the vibration data includes comparing the vibration data to a reference vibration data that was detected during an initial use of the bearing,
   determining the vibration stage flag includes determining the vibration stage flag based on a time-domain analysis of the vibration data and a frequency-domain analysis of the vibration data, and
   determining the vibration stage flag based on the frequency-domain analysis of the vibration data includes determining a frequency flag based on a maximum value of an analysis of at least two of a fundamental train frequency of the bearing, a ball pass outer race frequency, a ball pass inner race frequency, and a ball defect frequency.

2. The method of claim 1, wherein determining the vibration stage flag based on the time-domain analysis of the vibration data includes determining the vibration stage flag based on root mean square (RMS), Kurtosis, and Skewness values of the vibration data.

3. The method of claim 1, wherein determining the vibration stage flag further includes determining a time flag corresponding to the time-domain analysis of the vibration data and setting the vibration stage flag if either the time flag or the frequency flag is set.

4. The method of claim 1, wherein determining the vibration stage flag includes computing a resonance frequency and a frequency band of the resonance frequency, bandpass filtering the vibration data to obtain a filtered signal, demodulating the filtered signal to obtain a demodulated signal, and performing time-domain and frequency-domain analyses of the demodulated signal.

5. The method of claim 1, wherein determining the vibration stage flag based on the time-domain analysis of the vibration data includes normalizing the vibration data in a time domain, and wherein determining the vibration stage flag based on the frequency-domain analysis of the vibration data includes normalizing the vibration data in a frequency domain.

6. The method of claim 1, wherein:
  detecting the vibration data includes detecting vibration data from multiple vibration sensors; and
  determining the vibration stage flag based on the vibration data includes: determining a vibration stage flag based on the vibration data from each of the vibration sensors, and determining the vibration stage flag to be a maximum value of all of the vibration stage flags determined from each of the vibration sensors.

7. The method of claim 1, further comprising:
  storing, in a memory, a decision table; and
  determining, by the controller, a residual life of the bearing by comparing the combination of the vibration stage flag and the ODM data to the decision table.

8. A method for fault diagnosis of a bearing used in an engine, comprising:
  detecting, using an oil debris monitor (ODM) sensor, ODM data corresponding to an amount of debris flowing downstream from the bearing;
  detecting, using a vibration sensor, vibration data corresponding to vibration of the bearing during use;
  determining, by a controller, a vibration stage flag corresponding to a severity of damage of the bearing based on a time-domain analysis of the vibration data and a frequency-domain analysis of the vibration data;
  determining, by the controller, a severity level of the damage of the bearing based on a combination of the vibration stage flag and the ODM data; and
  outputting, by an output device, the severity level, wherein:
    determining the vibration stage flag based on the vibration data includes comparing the vibration data to a reference vibration data that was detected during an initial use of the bearing, and
    determining the vibration stage flag based on the frequency-domain analysis of the vibration data includes determining a frequency flag based on a maximum value of an analysis of at least two of a fundamental train frequency of the bearing, a ball pass outer race frequency, a ball pass inner race frequency, and a ball defect frequency.

9. The method of claim 8, wherein determining the vibration stage flag based on the time-domain analysis of the vibration data includes determining the vibration stage flag based on root mean square (RMS), Kurtosis, and Skewness values of the vibration data.

10. The method of claim 8, wherein determining the vibration stage flag further includes determining a time flag corresponding to the time-domain analysis of the vibration data, determining a frequency flag corresponding to the frequency-domain analysis, and setting the vibration stage flag if either the time flag or the frequency flag is set.

11. The method of claim 8, wherein determining the vibration stage flag includes computing a resonance frequency and a frequency band of the resonance frequency, bandpass filtering the vibration data to obtain a filtered signal, demodulating the filtered signal to obtain a demodulated signal, and performing time-domain and frequency-domain analyses of the demodulated signal.

12. The method of claim 8, wherein determining the vibration stage flag based on the time-domain analysis of the vibration data includes normalizing the vibration data in a time domain, and wherein determining the vibration stage flag based on the frequency-domain analysis of the vibration data includes normalizing the vibration data in a frequency domain.

13. The method of claim 8, wherein:
  detecting the vibration data includes detecting vibration data from multiple vibration sensors; and
  determining the vibration stage flag based on the vibration data includes: determining a vibration stage flag based on the vibration data from each of the vibration sensors, and determining the vibration stage flag to be a maximum value of all of the vibration stage flags determined from each of the vibration sensors.

14. A system for fault diagnosis of bearings, comprising:
  an oil debris monitor (ODM) sensor configured to detect ODM data corresponding to an amount of debris flowing downstream from a bearing;
  a vibration sensor configured to detect vibration data corresponding to vibration of the bearing during use;
  a controller configured to:
    determine a vibration stage flag corresponding to a severity of damage of the bearing based on the vibration data including comparing the vibration data to a reference vibration data that was detected during an initial use of the bearing, and
    determine a severity level of the damage of the bearing based on a combination of the vibration stage flag and the ODM data; and
  an output device configured to output the severity level, wherein:
    determining the vibration stage flag includes determining the vibration stage flag based on a time-domain analysis of the vibration data and a frequency-domain analysis of the vibration data, and
    determining the vibration stage flag based on the frequency-domain analysis of the vibration data includes determining a frequency flag based on a maximum value of an analysis of at least two of a fundamental train frequency of the bearing, a ball pass outer race frequency, a ball pass inner race frequency, and a ball defect frequency.

15. The system of claim 14, wherein the time-domain analysis of the vibration data is based on root mean square (RMS), Kurtosis, and Skewness values of the vibration data.

* * * * *